US010076733B2

(12) United States Patent
Morris et al.

(10) Patent No.: US 10,076,733 B2
(45) Date of Patent: Sep. 18, 2018

(54) UTILIZING WET FRACTURING SAND FOR HYDRAULIC FRACTURING OPERATIONS (71) Applicant: Evolution Well Services, LLC, The Woodlands, TX (US)

(72) Inventors: Jeffrey G. Morris, The Woodlands, TX (US); Adrian Benjamin Bodishbaugh, Fayetteville, AR (US); Michael Bateman, The Woodlands, TX (US); Neal Jensen, Henderson, NV (US)

(73) Assignee: Evolution Well Services, LLC, The Woodlands, TX (US)

( * ) Notice: Subject to any disclaimer, the term of this patent is extended or adjusted under 35 U.S.C. 154(b) by 0 days.

(21) Appl. No.: 15/452,415

(22) Filed: Mar. 7, 2017

(65) Prior Publication Data

US 2017/0259227 A1 Sep. 14, 2017

Related U.S. Application Data (60) Provisional application No. 62/305,449, filed on Mar. 8, 2016.

(51) Int. Cl.
*B01F 11/02* (2006.01)
*B01F 3/12* (2006.01)

(52) U.S. Cl.
CPC ........ *B01F 11/0266* (2013.01); *B01F 3/1242* (2013.01); *B01F 2215/0081* (2013.01)

(58) Field of Classification Search
CPC .............................. B01F 11/00; B01F 11/0266
USPC ..................................... 366/31, 32, 114, 115
See application file for complete search history.

(56) References Cited

U.S. PATENT DOCUMENTS

| 1,753,050 | A | * | 4/1930 | Hughes ..................... F23K 3/14 110/108 |
| 1,907,721 | A | * | 5/1933 | Booth et al. ........... B65D 88/66 366/114 |
| 3,113,621 | A | | 12/1963 | Krueger et al. |
| 3,147,144 | A | * | 9/1964 | Wilhelm ............. B29C 37/0071 118/308 |
| 3,187,958 | A | * | 6/1965 | Swart ..................... B65D 88/66 222/227 |
| 3,533,605 | A | * | 10/1970 | Futty et al. ........... B28C 7/0076 366/32 |
| 2004/0141412 | A1 | * | 7/2004 | Midas ................... B01F 9/0001 366/217 |
| 2010/0132949 | A1 | | 6/2010 | Defosse et al. |
| 2011/0073599 | A1 | | 3/2011 | Nieves |
| 2012/0255734 | A1 | | 10/2012 | Coli et al. |
| 2014/0027386 | A1 | | 1/2014 | Munisteri |

(Continued)

FOREIGN PATENT DOCUMENTS

CN 105363362 A 3/2016

OTHER PUBLICATIONS

PCT Int'l Search Report received in copending PCT Application No. PCT/US2017/021181 dated May 25, 2017, 10 pages.

*Primary Examiner* — David L Sorkin
(74) *Attorney, Agent, or Firm* — Blank Rome, LLP (57) ABSTRACT

A system and a method that utilizes wet proppants when creating fracturing fluid by receiving wet fracturing sand at a surge tank, vibrating the wet fracturing sand located within the surge tank, liquefying the wet fracturing sand within the surge tank based on the vibration, and metering the liquefied wet fracturing sand from the surge tank to a blending tub.

20 Claims, 10 Drawing Sheets

(56) References Cited

U.S. PATENT DOCUMENTS

2015/0240148 A1    8/2015   Luharuka et al.
2016/0349728 A1   12/2016   Oehring et al.
2017/0028368 A1    2/2017   Oehring et al.

* cited by examiner

UTILIZING WET FRACTURING SAND FOR HYDRAULIC FRACTURING OPERATIONS

CROSS-REFERENCE TO RELATED APPLICATIONS

This application claims the benefit of U.S. Provisional Patent Application No. 62/305,449, filed Mar. 8, 2016 by Jeffrey G. Morris et al. and entitled "Utilizing Wet Fracturing Sand for Hydraulic Fracturing Operations," which is hereby incorporated by reference as if reproduced in its entirety.

BACKGROUND

Hydraulic fracturing has been commonly used by the oil and gas industry to stimulate production of hydrocarbon producing wells, such as oil and/or gas wells. Hydraulic fracturing, sometimes called "fracing" or "fracking" is a process of injecting fracturing fluid, which is typically a mixture of water, proppants (e.g., sand, fracturing sand, ceramics and resin coated materials), and chemicals, into the wellbore to fracture the subsurface geological formations and release hydrocarbon reserves. The fracturing fluid is pumped into a wellbore at a sufficient pressure to cause fissures within the underground geological formations. Once inside the wellbore, the pressurized fracturing fluid flows into the subsurface geological formation to fracture the underground formation. The fracturing fluid may include water, various chemical additives, and proppants that promote the extraction of the hydrocarbon reserves, such as oil and/or gas. Proppants, such as fracturing sand, prevent fissures and fractures in the underground formation from closing, and for the formation to remain open so that hydrocarbon reserves are able to flow to the surface.

Hydraulic fracturing generally uses large amounts of sand (e.g., about five to fifty million pounds per well) to aid in the fracturing of wells. Prior to transport to the well site, the sand undergoes processing to: (1) remove impurities, (2) to dry the fracturing sand in order for it to meet American Petroleum Institute (API) recommended practices (i.e., RP 19C, 56, 58, and 60) and (3) to make it suitable for metering into the mixing process using conventionally employed hydraulic fracturing process equipment (e.g., fracturing blender) to produce a slurry or fracturing fluid. Mining and/or processing operators initially mine for fracturing sand within sand deposits that contain quartz grains with desired properties, such as relatively high crush strength and roundness. To satisfy fracturing criteria, the operators process the mined sand by washing it to remove impurities and subsequently drying the sand to remove moisture. Mining operators may then further filter out sand particles that fail to satisfy specific size criteria for fracturing operations. Once processing is complete, operators load and deliver the fracturing sand to well sites that may be hundreds of miles from the point of origin using specialized rail cars, trailers (e.g., hopper trailers and pneumatic vessels), and trucks that protect fracturing sand from environmental exposure. Operators use silos, domes, and other large and expensive storage vessels to store the dry sand at various points along the supply chain. Maintaining dry fracturing sand prior to mixing to form fracturing fluid increases an operator's ability to reliably control and meter the flow of fracturing sand. In contrast, wet fracturing sand normally clumps together causing its flow to be less consistent and more difficult to meter for fracturing purposes. Unfortunately, drying, transporting, and storing vast quantities of dry fracturing sand increases financial, operating, and logistical costs associated with fracturing operations.

SUMMARY

The following presents a simplified summary of the disclosed subject matter in order to provide a basic understanding of some aspects of the subject matter disclosed herein. This summary is not an exhaustive overview of the technology disclosed herein. It is not intended to identify key or critical elements of the invention or to delineate the scope of the invention. Its sole purpose is to present some concepts in a simplified form as a prelude to the more detailed description that is discussed later.

In one embodiment, a system for utilizing wet proppants when creating fracturing fluid, comprising: a surge tank, a vibration component disposed with the surge tank and configured to liquefy wet proppants received by the surge tank, and a metering system coupled to the surge tank, wherein the metering system is configured to control an amount of the liquefied wet proppants that is outputted to a blending tub.

In another embodiment, a method for utilizing wet proppants when creating fracturing fluid, the method comprising: receiving wet fracturing sand at a surge tank, vibrating the wet fracturing sand located within the surge tank, liquefying the wet fracturing sand within the surge tank based on the vibration, and metering the liquefied wet fracturing sand from the surge tank to a blending tub.

In yet another embodiment, a surge tank for utilizing wet proppants when creating fracturing fluid comprising: a vibration component affixed to an outer surface of the surge tank to cause vibration of wet proppants that enter the surge tank and an auger coupled to the surge tank, wherein the auger is configured to meter liquefied wet proppants output into a blending tub.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

While certain embodiments will be described in connection with the illustrative embodiments shown herein, the invention is not limited to those embodiments. On the contrary, all alternatives, modifications, and equivalents are included within the spirit and scope of the invention as defined by the claims. In the drawing figures, which are not to scale, the same reference numerals are used throughout the description and in the drawing figures for components and elements having the same structure, and primed reference numerals are used for components and elements having a similar function and construction to those components and elements having the same unprimed reference numerals.

DETAILED DESCRIPTION

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts or suffixes are understood to reference all instance of subscripts and suffixes corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

The terms "a," "an," and "the" are not intended to refer to a singular entity unless explicitly so defined, but include the general class of which a specific example may be used for illustration. The use of the terms "a" or "an" may therefore mean any number that is at least one, including "one," "one or more," "at least one," and "one or more than one." The term "or" means any of the alternatives and any combination of the alternatives, including all of the alternatives, unless the alternatives are explicitly indicated as mutually exclusive. The phrase "at least one of" when combined with a list of items, means a single item from the list or any combination of items in the list. The phrase does not require all of the listed items unless explicitly so defined.

The term "fracturing sand," as used within this disclosure, serves as a non-limiting example of a proppant used as a component of fracturing fluid. "Fracturing sand" is also used herein to collectively refer to both wet and dry fracturing sand. Embodiments in this disclosure are not limited to fracturing sand and any other type of proppant, such as man-made ceramics, aluminum beads and sintered bauxite, can be used with the various embodiments presented in the disclosure. Unless otherwise specified within the disclosure, the term "fracturing sand" can be interchanged with and considered synonymous throughout this disclosure with the term "proppants."

As used herein, the term "wet fracturing sand" refers to a quantity of fracturing sand that contains a moisture content of about one percent or more, which is typically determined based on weight. The term "dry fracturing sand" refers to quantities of fracturing sand that contain a moisture content of less than about one percent.

As used herein, the term "liquefying wet fracturing sand" refers to enhancing and transforming the flow properties of wet fracturing sand to be substantially similar to dry fracturing sand in order to accurately control the amount of metered fracturing sand. For example, wet fracturing sand can liquefy and have flow properties similar to dry fracturing sand with the assistance of mechanical forces and/or sound waves.

As used herein, the term "transport" refers to any transportation assembly, including, but not limited to, a trailer, truck, skid, rail car, and/or barge used to transport relatively heavy structures and/or other types of articles, such as fracturing equipment and fracturing sand.

As used herein, the term "trailer" refers to a transportation assembly used to transport relatively heavy structures and/or other types of articles, such as fracturing equipment and fracturing sand that can be attached and/or detached from a transportation vehicle used to pull or move the trailer. In one embodiment, the trailer may include mounts and manifold systems to connect the trailer to other fracturing equipment within a fracturing system or fleet.

Unless otherwise specified within the disclosure, the term "surge tank" can be interchanged with and considered synonymous throughout this disclosure to the term "hopper."

Various example embodiments are disclosed herein that deliver and/or utilize wet fracturing sand for fracturing operations at one or more well sites. Rather than drying and/or transporting dry fracturing sand to a well site for fracturing operations, fracturing sand may be transported to a well site for fracturing operators without using specialized transport (e.g., dry bulk tank trailers) or transportation containers designed to prevent exposure to rain, moisture, and/or other environmental factors that impact the dryness level of the fracturing sand. Once the transports deliver the fracturing sand to the well site, well-site operators are able to store the fracturing sand without using specialized storage facilities and/or containers (e.g., storage silos) that maintain the relatively low moisture levels required in dry fracturing sand. To produce the fracturing fluid at the well site, the fracturing sand may be moved from a storage site using one or more mechanical means (e.g. front end loaders) that provide the fracturing sand to a conveyor system. The conveyor system subsequently delivers the fracturing sand to a surge tank (e.g., a blender hopper). To process fracturing sand with varying moisture content levels, the surge tank comprises a plurality of vibration components that are adapted to break bonds (e.g., cohesive bonds) created from the surface tension of water that affix particles in fracturing sand together. In one embodiment, the vibration components provide mechanical vibration forces that directly agitate the wet/dry fracturing sand. Additionally, or alternatively, the vibration components provide mechanical vibration forces that agitate the surge tank assembly containing the fracturing sand. In another embodiment, the vibration component generates sound waves that traverse the surge tank to separate fracturing sand particles. Once separated, a metering system (e.g., one or more augers) may control and meter the fracturing sand into a blending module (e.g., a blender tub) to produce fracturing fluid.

Figure 1:
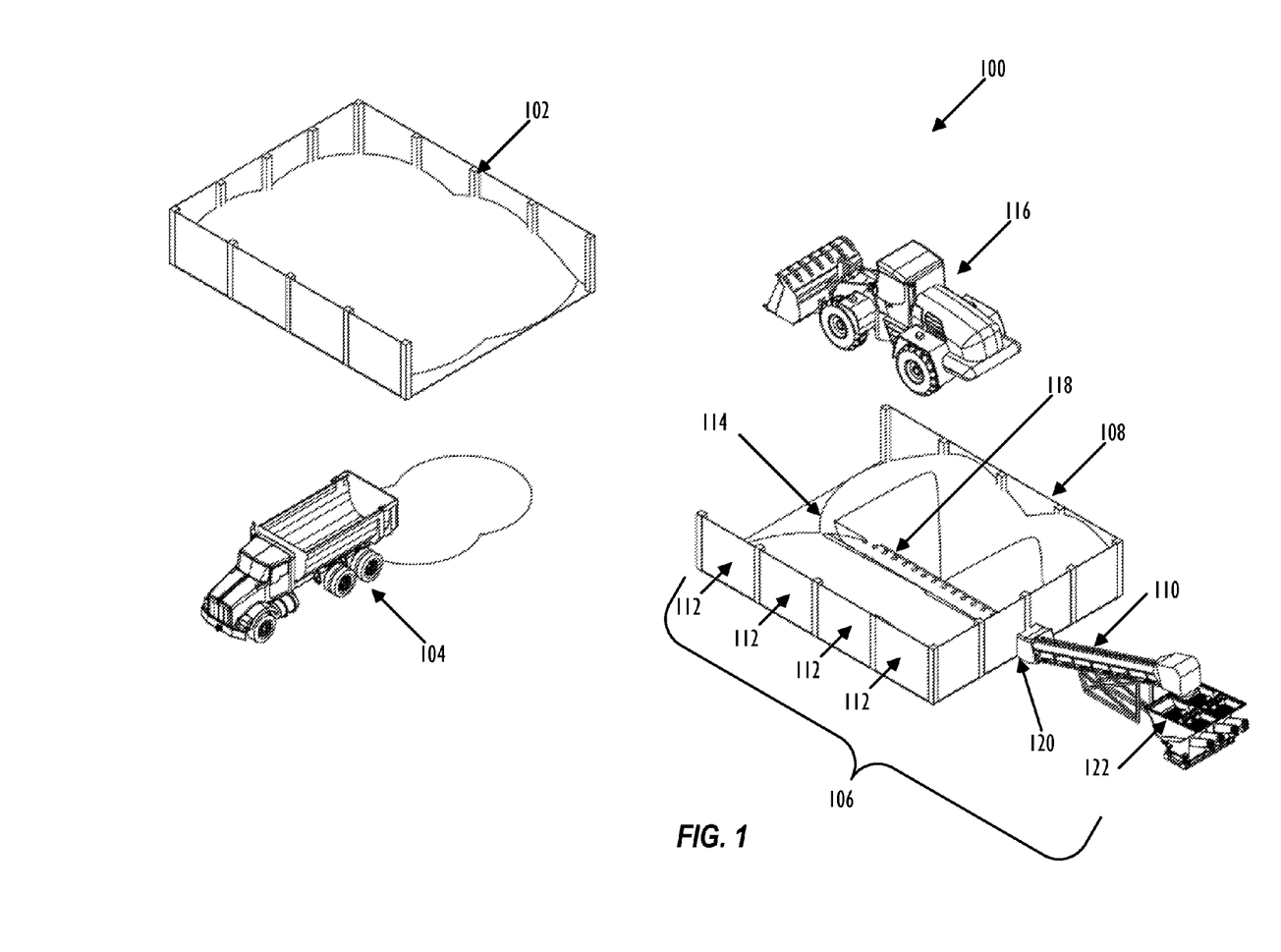
FIG. 1 is a schematic diagram of an embodiment of a well site that includes a wet fracturing sand agitation system capable of moving and liquefying wet fracturing sand utilized for producing fracturing fluid.

FIG. 1 is a schematic diagram of an embodiment of a well site 100 that includes a wet fracturing sand agitation system capable of moving and liquefying wet fracturing sand for mixing with fracturing fluid. The well site 100 comprises one or more well heads (not illustrated in FIG. 1) that the wet fracturing sand agitation system is setup as a component, portion, and/or subsystem of a fracturing system. Initially, to produce fracturing fluid for fracturing the wells, vendors transport proppants, such as fracturing sand, to the well site 100 using a variety of transportation methods, such as trucks, trailers, rail cars, and/or shipping vessels. In one embodiment, the fracturing sand is delivered to the well site as wet fracturing sand without using specialized containers and/or equipment to maintain a designated moisture level for a dry bulk load. By doing so, operators may be able to reduce product, transportation, and/or storage costs associated with delivering dry fracturing sand to a well site for fracturing operations. Although the wet fracturing sand agitation system used in FIG. 1 is capable of mixing wet fracturing sand with fracturing fluid, the wet fracturing sand agitation system is not limited to using wet fracturing sand and could be compatible with processing dry fracturing sand.

The well site 100 may include one or more fracturing sand storage sites 102. Transports 104 (e.g., a conventional dump truck) may move fracturing sand from offsite and/or other onsite locations to the fracturing sand storage sites 102. In one embodiment, to reduce well site costs, the fracturing sand storage sites 102 do not include enclosed boxes, containers, storage silos, and/or other storage systems (e.g., fracturing sand storage trailers) designed to prevent exposing dry bulk loads (e.g., dry fracturing sand) to moisture. Instead, the fracturing sand storage sites 102 include uncovered containers and/or uncovered piles of fracturing sand. Additionally, or alternatively, rather than vacuuming or using other means to prevent the release of silica dust caused from storing and handling the fracturing sand, operators may use a liquid spray system to maintain a pre-determined moisture level range for wet fracturing sand stored at the fracturing sand storage sites 102. Introducing moisture into fracturing sand to bind the sand particles together could reduce/prevent the release of silica dust into the air while reducing operating costs.

Operators may move fracturing sand from the fracturing sand storage sites 102 onto a conveyor system 106 using one or more front end loaders 116, other transports 104, and/or other mechanical means known by persons of ordinary skill in the art. The conveyor system 106 is adapted to receive the fracturing sand and move the fracturing sand to the surge tank 122. The conveyor systems 106 may include a variety of transloading equipment, such as conveyor belts, conveyor loaders, augers, bucket systems, screw conveyors and/or pneumatic conveyors powered by diesel/gas engines, other mechanical means, and/or electrical means known by persons of ordinary skill in the art. The conveyor system 106 may be adapted to deliver fracturing sand at a predetermined rate to the surge tank 122. The amount of fracturing sand the conveyor system 106 delivers to the surge tank may fall within a tolerance range since the surge tank 122 is capable of handling surges or degrees of variance on the amount of input fracturing sand. For example, conveyor system 106 could be adapted to deliver up to about 20,000 pounds (lbs) of sand per minute. The amount of fracturing sand delivered by the conveyor system 106 could depend on the amount of fracturing sand the surge tank 122 is set to process and/or meter into a blender tub of a fracturing blending module. For example, the conveyor system 106 may be configured to synchronize with surge tank 122 to deliver enough fracturing sand to compensate for rate change increases or decreases associated with pumping fracturing fluid into a well. In this instance, the conveyor system 106 could compensate for rate change increase by delivering fracturing sand at a rate greater than 20,000 lbs of sand per minute.

In one embodiment, the conveyor system 106 includes a conveyor storage container 108 that temporarily stores the fracturing sand and assists in transferring fracturing sand to a conveyor assembly 110. To improve mobility of the conveyor storage container 108, the fracturing sand storage container 108 may comprise a plurality of container segments 112 (including pads and sidewalls) that are connected together. FIG. 1 illustrates an embodiment of a conveyor storage container 108 that comprises four different container segments 108, where three ends of the conveyor storage container 108 are propped up to build side walls. Entrance 114 of the conveyor storage container 108 allows for a front end loader 116 or other transport 104 to enter, move and/or place sand within the conveyor storage container 108. The conveyor storage container 108 may include a conveyor transport component 118 that moves fracturing sand stored in the conveyor storage container 108 to the conveyor assembly 110. The conveyor storage container 108 and conveyor assembly 110 may be connected via a connection well 120. The conveyor assembly 110 may then transport the fracturing sand to the surge tank 122. Other embodiments of the conveyor system 106 may use different conveyor storage containers 108 and/or conveyor assembly 110 to move and transfer fracturing sand, for example, the mobile conveyor system 500 as described in FIGS. 5A and 5B.

When the fracturing sand reaches the surge tank 122, the surge tank 122 reduces clumping of the wet fracturing sand by breaking bonds (e.g., cohesion bonds) between water and the fracturing sand particles. The surge tank 122 can be configured to break the bonds using one or more vibrator components to liquefy the wet fracturing sand and reduce sand clumping. The surge tank 122 may receive from the conveyor system 106 wet fracturing sand that is relatively difficult to meter and control when directly supplying the fracturing sand to a hydraulic fracturing blender tub. By using vibrator components to liquefy the sand, the surge tank 122 is able to enhance the flow properties of wet fracturing sand in order to accurately control the amount of metered fracturing sand.

In one embodiment, the vibrator components directly vibrate and screen the wet fracturing sand while minimizing vibration forces experienced by the surge tank 122. Additionally, or alternatively, one or more of the vibrator components can be adapted to generate a mechanical shaking force on the surge tank 122 to break the cohesion bonds of the wet fracturing sand. In another embodiment, the vibrator components are adapted to generate sound waves that cause vibrations within the wet fracturing sand to break the cohesion bonds. Other types of vibration components known to the art may be used as desired, and combinations of different types of vibration components may be used. A metering system, such as an auger, a gate, a venturi, and/or any other metered conveyor known by persons of ordinary skill in the art, may then meter the liquefied fracturing sand into a blending module (e.g., a blender tub). A blending module may then mix the controlled amount of wet fracturing sand with other fluids to generate fracturing fluid.

The vibrator components may be powered by a variety of power sources that include, but are not limited to, air pressure, hydraulics, and/or electricity. Pneumatic and hydraulic vibrators may be controlled by adjusting the air and hydraulic pressures, respectively. In one embodiment, to power the pneumatic and/or hydraulic vibrators, one or more diesel/gas engines and/or other mechanical means may be used as a power source. In other embodiments where the vibrator components are powered by electricity, operators may use electric motors and electric drives (e.g., variable frequency drives) to control the vibration intensity and/or duration of the vibration either directly or indirectly. For example, one or more vibrator components may be powered using hydraulics systems that are powered by one or more electric motors. Specifically, the electric motors are used to power hydraulic pumps to provide the hydraulic pressure used to operate the vibrator components. By controlling the electric motors, an operator is able to indirectly control the one or more vibrator components via the hydraulic pressure. In another example, operators are able to control the one or more vibrator components directly by connecting one or more electric motors to one or more vibrator components. Adjusting the electric motors' attributes, such as frequency, voltage, and/or amperage could vary operation of the vibrator components.

The surge tank 122 depicted in FIG. 1 is applicable to any blending operation for mixing and producing fracturing fluid. In particular, the surge tank 122 may be mounted on conventional blender modules powered by diesel/gas engines, pneumatic, electric blender modules, and/or other well-known hydraulic fracturing blending equipment and/or transports. As a non-limiting example, the surge tank 122 may be mounted on a dual configuration electric blender that comprises electric motors for the rotating machinery located on a single transport, which is described in more detail in U.S. Pat. No. 9,366,114, filed Apr. 6, 2012 by Todd Coli et al. and entitled "Mobile, Modular, Electrically Powered System for use in Fracturing Underground Formations," ('114 patent) which is herein incorporated by reference in its entirety. Additionally, the surge tank 122 may be mounted to blending modules that have been modified to incorporate other hydraulic fracturing equipment onto a single transport. For example, surge tank 122 may be a mounted on a trailer configured to combine a blender unit with a hydration unit. In another example, the surge tank 122 may be mounted on a trailer that combines a blender unit, a hydration unit, and a sand storage unit. Other embodiments of the surge tank 122 could be a stand-alone unit that is mounted on its own transport or a stationary unit that is built on the well site.

To reduce vibration and disturbances of other fracturing processes, the surge tank 122 may include a vibration isolation system that include springs, air bags, rubber-based dampeners (e.g., rubber bushings), and/or other vibration isolation components. The vibration isolation system may be configured to reduce the amount vibration experienced by other blender module components that could be mounted on the same transport. For example, if the vibrator components mechanically cause the surge tank 122 to continuously or periodically vibrate and shake, the vibration isolation system absorbs and dampens the mechanical vibration energy to avoid transfer of mechanical vibration energy that could potentially damage other blender module components, such as the blender tub and manifolds that are also mounted on the same transport. In embodiments where a vibration screen and/or sound waves are used to directly liquefy sand without vibrating the surge tank 122, the vibration isolation system may dampen and reduce the amount of vibration experienced by the surge tank 122. Utilizing a vibration isolation system to dampen vibration from a vibration screen is discussed in more detail in FIGS. 4A and 4B.

Although FIG. 1 illustrates that the fracturing sand storage site 102 do not directly deliver fracturing sand to the surge tank 122, other embodiments of the wet fracturing sand agitation system can have fracturing sand storage sites 102 that include bulk storage tanks, such as silos or bins that allow the fracturing sand to directly feed or convey into the surge tank 122. The bulk storage tanks within the fracturing sand storage sites 102 may move the fracturing sand via gravity, conveyor belts, bucket elevators, augers, and/or other mechanical means known by persons of ordinary skill in the art to the surge tank 122. Using FIG. 1 as an example, rather than have the conveyor system 106 directly supply wet fracturing sand into the surge tank 122, the conveyor system 106 can supply wet fracturing sand to a fracturing sand storage site 102 that is elevated above the surge tank 122. In another example, the wet fracturing sand agitation system may not include a separate conveyor system 106, and instead replaces the separate conveyor system 106 with a fracturing sand storage site 102 elevated above the surge tank 122. In both examples, the fracturing sand storage site 102 may use gravity to directly feed into the surge tank 122.

Figure 7:
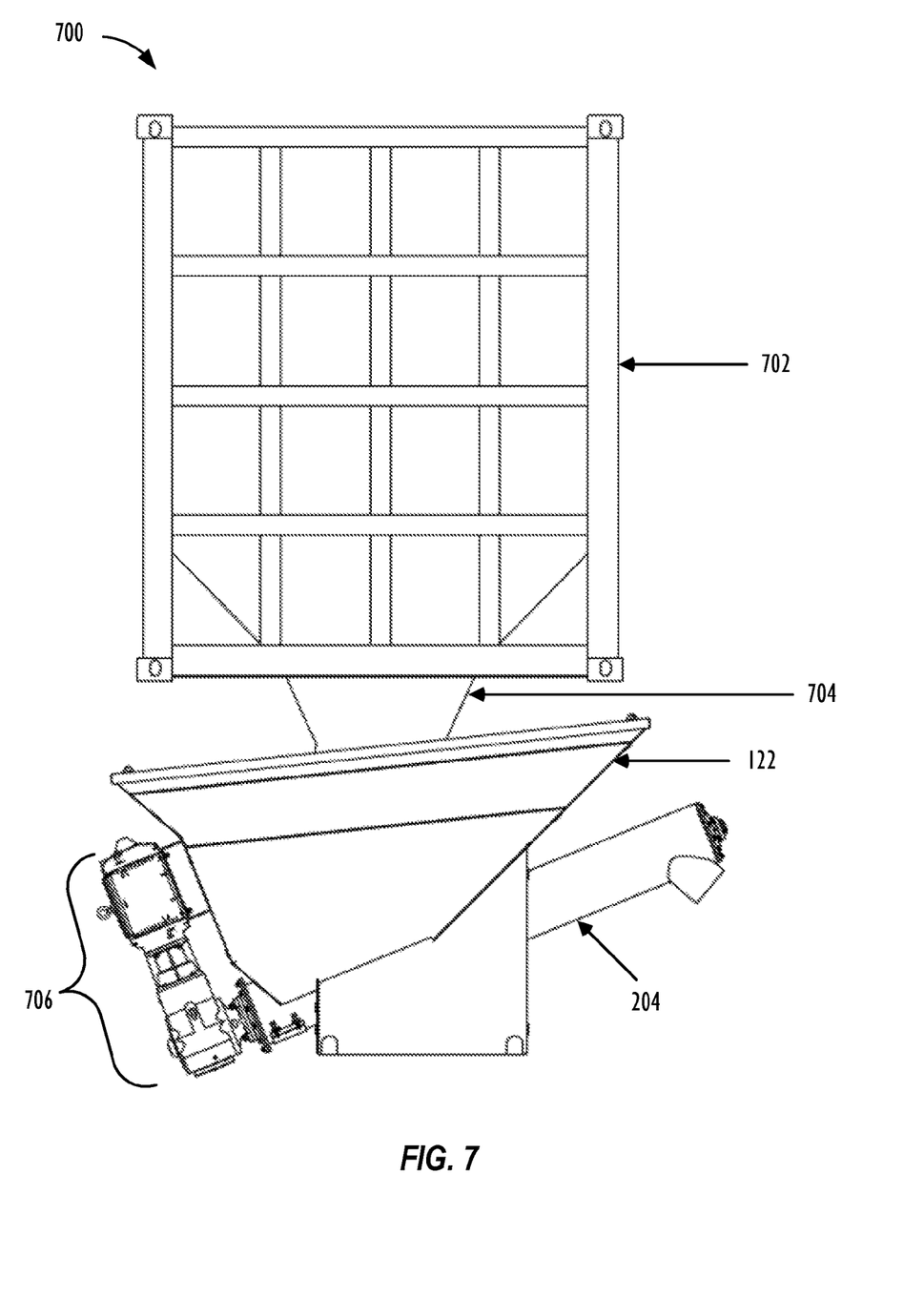
FIG. 7 is a schematic diagram of an embodiment of a wet fracturing sand agitation system that includes a bulk storage tank positioned above the surge tank.

FIG. 7 is a schematic diagram of an embodiment of a wet fracturing sand agitation system 700 that includes a bulk storage tank 702 positioned above the surge tank 122. Recall that in FIG. 1, the bulk storage tank 702 may be part of fracturing sand storage site 102. In one embodiment, the bulk storage tank 702 includes one or more vibrator components (not shown in FIG. 7) similar to the vibrating components as discussed above for the surge tank 122. Including the vibrator components with the bulk storage tank 702 further assists in reducing the clumping of the wet fracturing sand and liquefying the wet fracturing sand. As shown in FIG. 7, the bulk storage tank 702 directly feeds into the surge tank 122 using gravity. A spout 704, such as a rubber boot, funnels the wet fracturing sand into the top opening of the surge tank 122. As the surge tank 122 liquefies the wet fracturing sand, a prime mover 706 (e.g., an electric motor) drives the metering system 204 to meter the liquefied wet fracturing sand into one or more blending modules.

Figure 2:
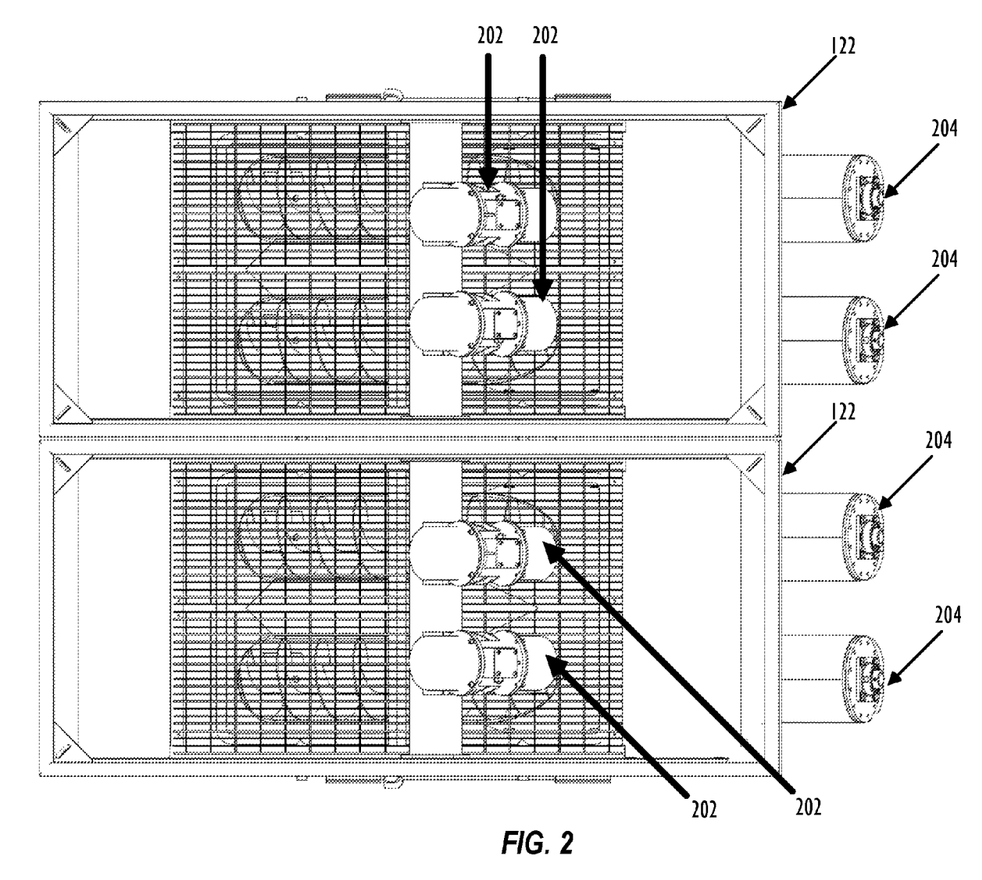
FIG. 2 illustrates a top-down view of an embodiment of a surge tank that comprises a plurality of vibrating components.

FIG. 2 illustrates a top-down view of an embodiment of a surge tank 122 that comprises a plurality of vibrating components 202. In FIG. 2, two surge tanks 122 are mounted side-by-side to provide fracturing sand to a dual configuration blender as described in more detail in the '114 patent and U.S. Pat. No. 9,534,473, filed Dec. 16, 2015 by Jeffrey G. Morris et al. and entitled "Mobile Electric Power Generation for Hydraulic Fracturing of Subsurface Geological Formations," (the '473 patent) which is also incorporated by reference in its entirety. In other embodiments, a single surge tank 122 or more than two surge tanks 122 may be used to provide fracturing sand to other types of blender modules (e.g., a single surge tank 122 providing fracturing sand to a conventional diesel blender module).

For each of the surge tanks 122, vibrating components 202 may be mounted at one or more locations of the surge tank 122 to generate mechanical vibration forces that agitate the surge tank 122. Using FIG. 2 as an example, the vibrating components 202 are mounted on top or affixed to an outer top surface of the surge tank 122. In FIG. 2, the vibrating components 202 are mounted or affixed above the opening where fracturing sand enters surge tank 122. The vibrating components 202 generate vibration forces aimed to break bonds between water and fracturing sand particles. Other embodiments of the surge tanks 122 may include vibrating components 202 placed at other locations of the surge tank, such as the side walls and/or bottom of the surge tank 122. Each of the vibrating components 202 may be configured to generate mechanical forces that shake at least a portion of the surge tank 122 and/or the wet sand independently at relatively high frequencies. For example, each of the vibrating components 202 may comprise one or more, electric motors (e.g. an electromagnetic motor), mechanical, pneumatic, and/or hydraulic means that move a set of weights to provide the mechanical vibration force to agitate the surge tank 122.

Each of the surge tanks 122 may comprise one or more metering systems 204 that meter the wet fracturing sand into one or more blender modules (e.g., a blending tub). As shown in FIG. 2, the metering systems 204 are coupled to the bottom of each of the surge tanks 122. In FIG. 2, the metering systems 204 are augers that are positioned at an incline to meter the liquefied wet fracturing sand to the blender modules. In other embodiments of the surge tanks 122, the metering systems 204 may be positioned in a straight or horizontal orientation. Correctly controlling and metering the liquefied wet fracturing sand into the blender modules affects the overall proppant concentration of the fracturing fluid (e.g., weight of the slurry). Controlling the overall proppant concentration is advantageous because the overall proppant concentration could affect the proppant transport and the propped fracture dimensions of the subsurface geological formations and the realization of the hydraulic fracturing treatment.

Figure 3A:
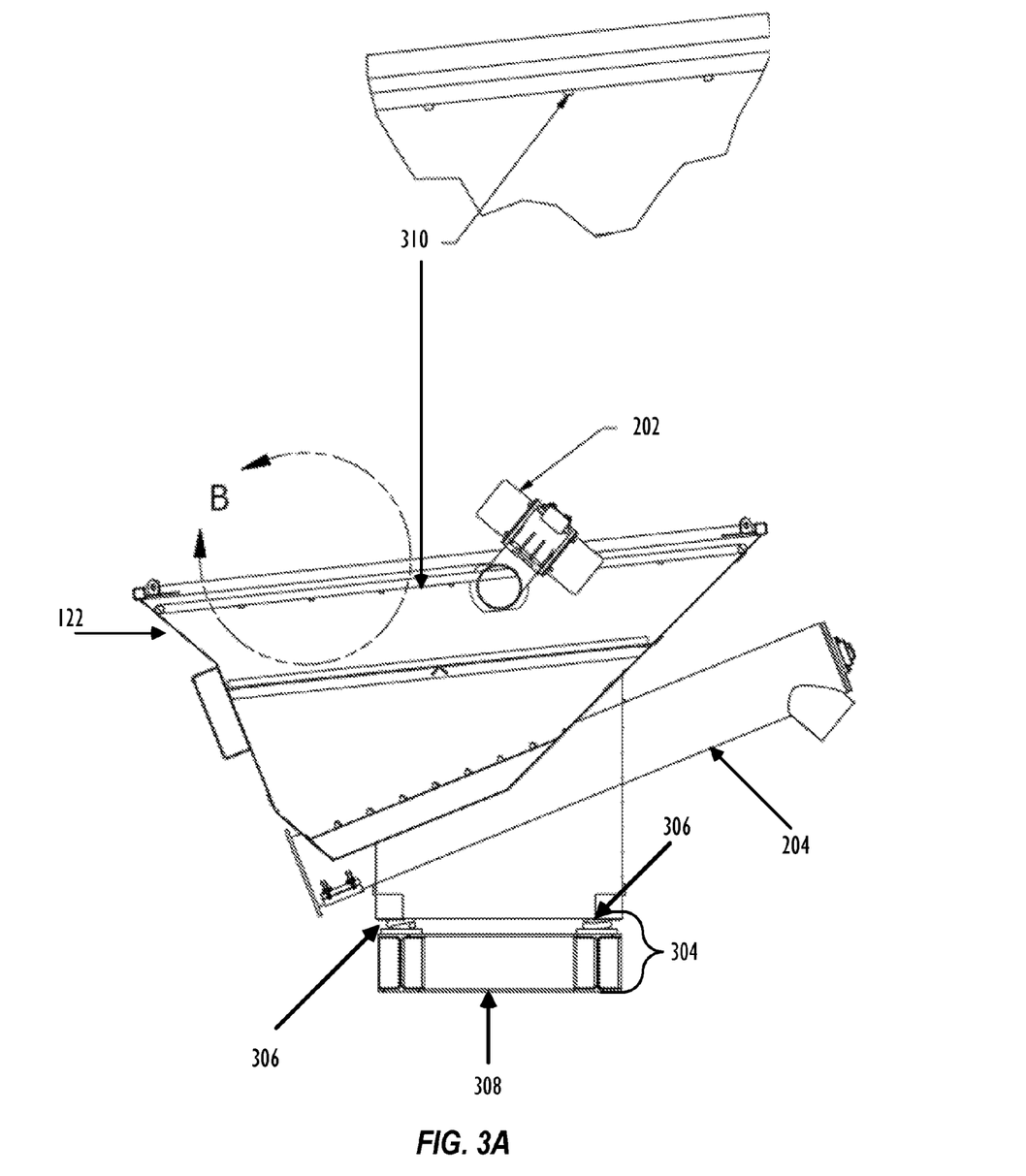
FIG. 3A illustrates a side view of an embodiment of a surge tank that comprises a plurality of vibrating components and a vibration isolation system.

FIG. 3A illustrate a side view of an embodiment of a surge tank 122 that comprises vibrating components 202 and a vibration isolation system 304. The vibration isolation system 304 comprises a vibration isolator 306 and a structure base 308. As shown in FIG. 3A, the vibration isolator 306 is a vibration damping spring that prevents other fracturing equipment (e.g., drives, motors, and pumps) located on the same transport from being affected by the vibration. Other embodiments of the vibration isolation system 304 may use and/or include other types of vibration isolators 306, such as air bags, rubber-based dampeners and any combination thereof. The structure base 308 acts as a platform used to support the surge tank 300 and the vibration isolators 306.

To regulate the moisture content of the wet fracturing sand, FIG. 3A illustrates that the surge tanks 122 comprises a spray system configured to provide water to maintain and/or adjust the moisture content of the wet fracturing sand. In one embodiment, the spray system includes a spray bar 310 at the top of the surge tank 122 and/or near the opening of where a conveyor transfers the fracturing sand to the surge tank 122. The spray bar 310 applies liquid, such as water, friction reducers, fracturing fluid, and/or other chemical and additives used to produce fracturing fluid, to moisturize the wet fracturing sand held within the surge tank 122. The spray bar 310 can also provide the benefit of reducing the amount of silica dust released into the surrounding air and environment; thereby, reducing the risk of personal injury or death from the inhalation of silica dust. In another embodiment, in addition or alternative to using spray bars 310, the surge tank 122 includes perforated/jet spray piping (not shown in FIG. 3A) located within a surge tank 122 container that targets and moistures fracturing sand located in different areas of the surge tank 122. The perforated/jet spray piping may be capable of providing liquid content, such as spraying the liquid, within the surge tank 122. In addition, the spray bar 310 and/or perforated/jet spray piping may generate a pre-determined depth of liquid within the surge tank 122 to liquefy the wet fracturing sand. The spray system may also be adapted to spray air to assist in liquefying the wet fracturing sand.

Figure 3B:
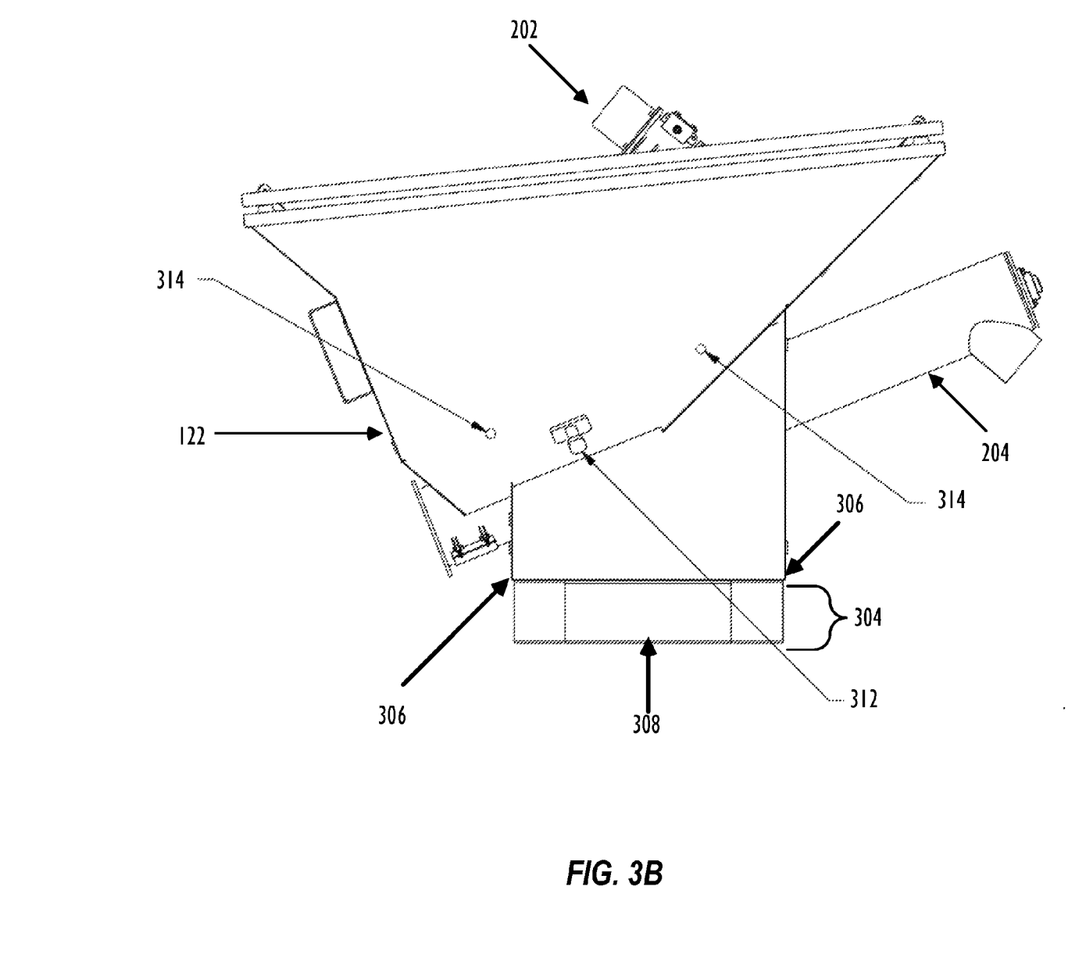
FIG. 3B illustrates a side view of an embodiment of a surge tank that comprises a plurality of vibrating components and a vibration isolation system.

FIG. 3B illustrates a side view of another embodiment of a surge tank 122 that comprises vibrating component 312 and water/air inlet 314. FIG. 3B illustrates that the surge tank 122 includes a vibration component 312, such as a pneumatic vibrator or piston vibrator, located near the metering system 204 (e.g., auger). The vibration component 312 is affixed to the outer surfaces of the surge tank 122 and is located near or proximate to the metering system 204. Affixing the vibration component 312 at the bottom of the surge tank 122 and proximate to the metering system 204 allows the vibration component 312 to provide mechanical forces that agitate the bottom of the surge tank 122 prior to the fracturing sand entering the metering system 204. Although FIG. 3B illustrates that the vibrating components 312 located at the bottom and/or proximate to the metering system 204 work in conjunction with vibrating components 202 affixed to the top of the surge tank 122, other embodiments of the surge tank 122 may include the vibrating components 312 near the metering system 204 without using the vibrating components 202 located at the top of the surge tank 122. In FIG. 3B, the water/air inlet 314 is an inlet that supplies water and/or air to the spray bar 310 as shown in FIG. 3A and/or the perforated/jet spray piping located within the surge tank 122

Figure 4A:
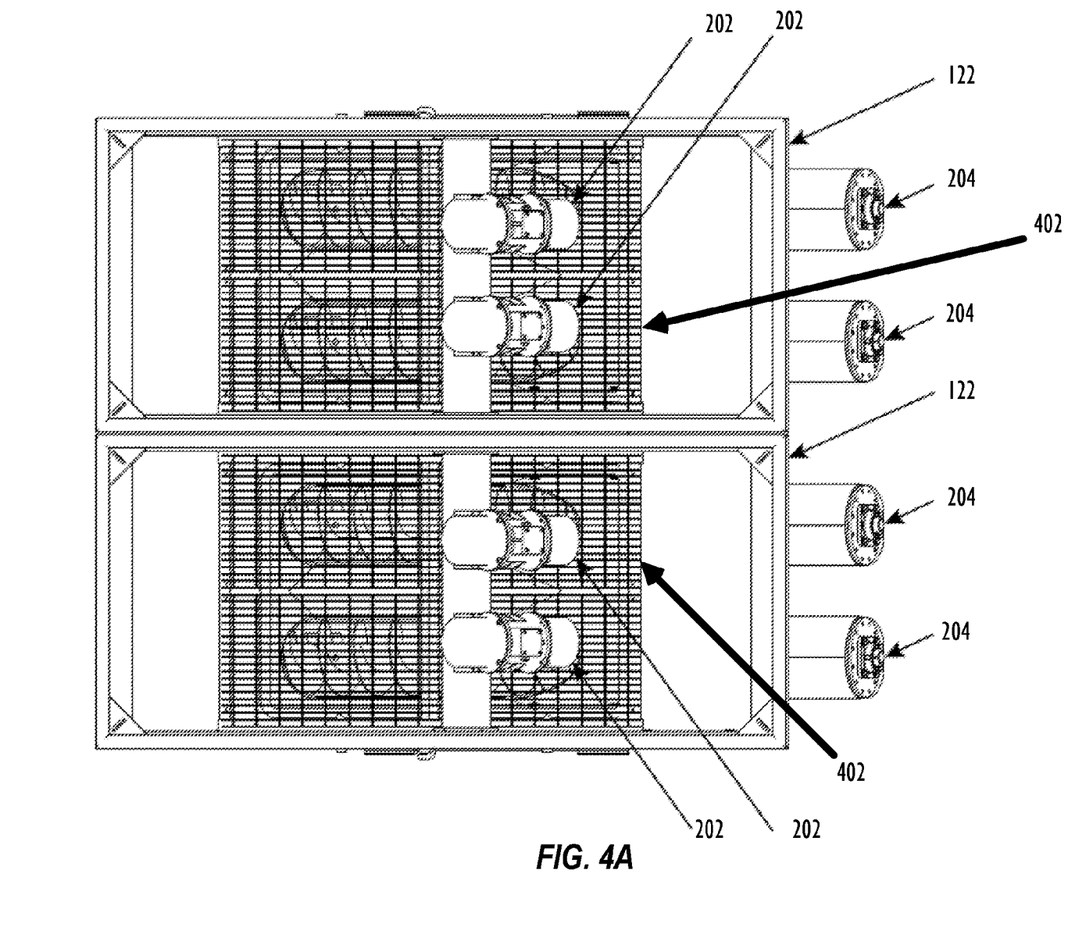
FIG. 4A illustrates a top-down view of an embodiment of a surge tank that comprises an internal vibrating component.

FIG. 4A illustrates a top-down view of an embodiment of a surge tank 122 that comprises an internal vibrating component 402. FIG. 4A illustrates that in addition to including vibrating components 202 located at the top of the surge tank 122, one or more internal vibrating components 402 may be located within the within the surge tank 122 that independently vibrate the fracturing sand without vibrating the surge tank 122. The internal vibrating component 402 may include a vibrating screen affixed within the surge tank 122 such that when wet fracturing sand passes through the vibrating screen, the mechanical vibration forces break apart the bonds to liquefy the sand. The surge tank 122 may also include a vibration isolation system (e.g., rubber-based dampers) that isolate and prevent transferring of mechanical vibration forces generated from the internal vibrating component 402 to the surge tank 122. In another embodiment, rather than using an internal vibrating component 402 positioned within the surge tank 122, one or more vibrating components may each include a vibrating screen that is placed over the surface and at the entrance of the surge tank 122. This way, the vibrating component will assist in liquefying wet fracturing sand prior to entering the surge tank 122.

In another embodiment, the internal vibrating components 402 may be configured to generate and project sound waves (e.g., frequency can vary being subsonic, sonic or ultrasonic waves) into the wet fracturing sand collected within the surge tanks 122. As the sound waves travel through the wet fracturing sand, the sound waves vibrate and break apart bonds between water and/or the fracturing sand particles. In one embodiment, the internal vibrating components 402 could be placed in a grid-like or an array arrangement where each of the vibrating components 402 target one or more portions of the wet fracturing sand collected within the surge tank 122. The frequency and amplitude generated by the internal vibrating components 402 to liquefy sand may depend on a variety of factors that include, but are not limited to the moisture content level, sand particle size, and/or sand particle density. For example, the frequency of the internal vibrating components 402 may be cycled and/or implemented in-phase or out-phase to generate the appropriate sound waves.

Figure 4B:
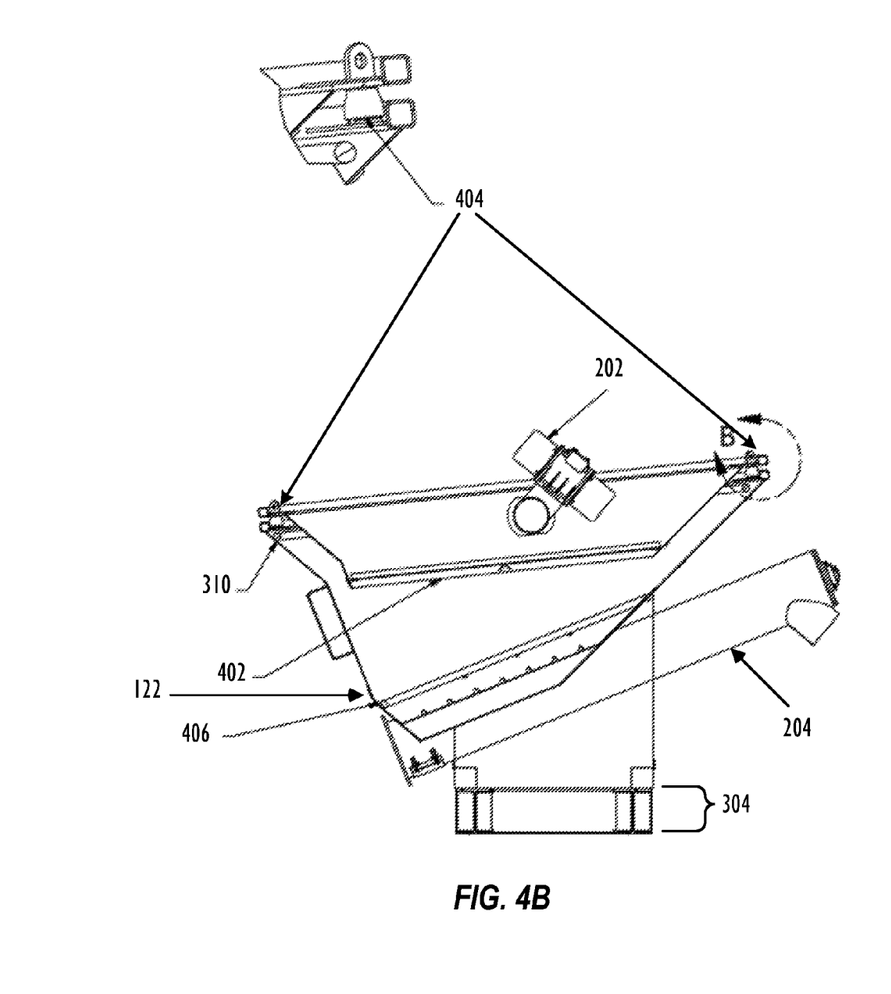
FIG. 4B illustrates a side view of an embodiment of a surge tank that includes an internal vibrating component and vibration isolation system.

FIG. 4B illustrates a side view of an embodiment of a surge tank 122 that includes an internal vibrating component 402 and surge tank isolation components 404. As shown in FIG. 4B, the internal vibrating component 402 is positioned between the opening of the surge tank 122 and the metering system 204. The top of the surge tank 122 includes surge tank isolation components 404 that dampen vibration generated from the internal vibrating components 402. In FIG. 4B, the surge tank isolation components 404 may be used in conjunction with the vibration isolation system 304 as described in FIG. 3B to dampen and isolate vibration forces.

FIG. 4B also illustrates that the surge tank 122 includes a perforated/jet spray piping 406 regulate the moisture content of the wet fracturing sand. The perforated/jet spray piping 406 is located within the surge tank 122 to target and provide moisture to different areas of the surge tank 122. Recall that the perforated/jet spray piping may be capable of providing liquid content, such as spraying the liquid, within the surge tank 122. In some instances, the spray bar 310 and/or perforated/jet spray piping 406 may generate a pre-determined depth of liquid within the surge tank 122 to liquefy the wet fracturing sand. Both the spray bar 310 and perforated/jet spray piping 406 may also be adapted to spray air to assist in liquefying the wet fracturing sand. Although FIG. 4B illustrates that the surge tank 122 includes both the spray bar 310 and perforated/jet spray piping 406, other embodiments of the surge tank 122 can include the perforated/jet spray piping 406 without the spray bar 310 or vice-versa.

Figure 5A:
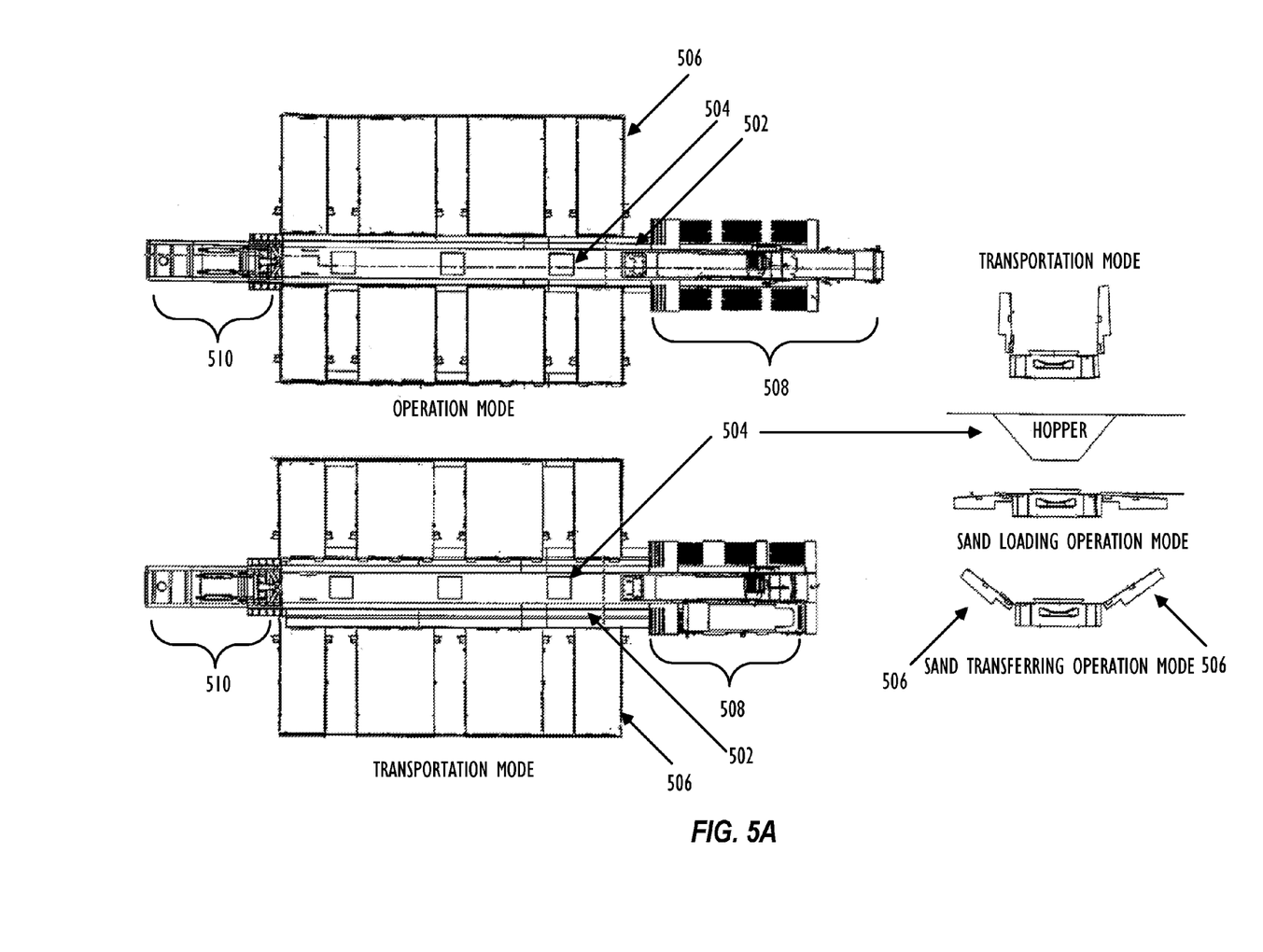
FIG. 5A illustrates a top-down view of an embodiment of a mobile conveyor system adapted to allow fracture sand transports to drive up to and directly load fracturing sand onto the mobile conveyor system.
Figure 5B:
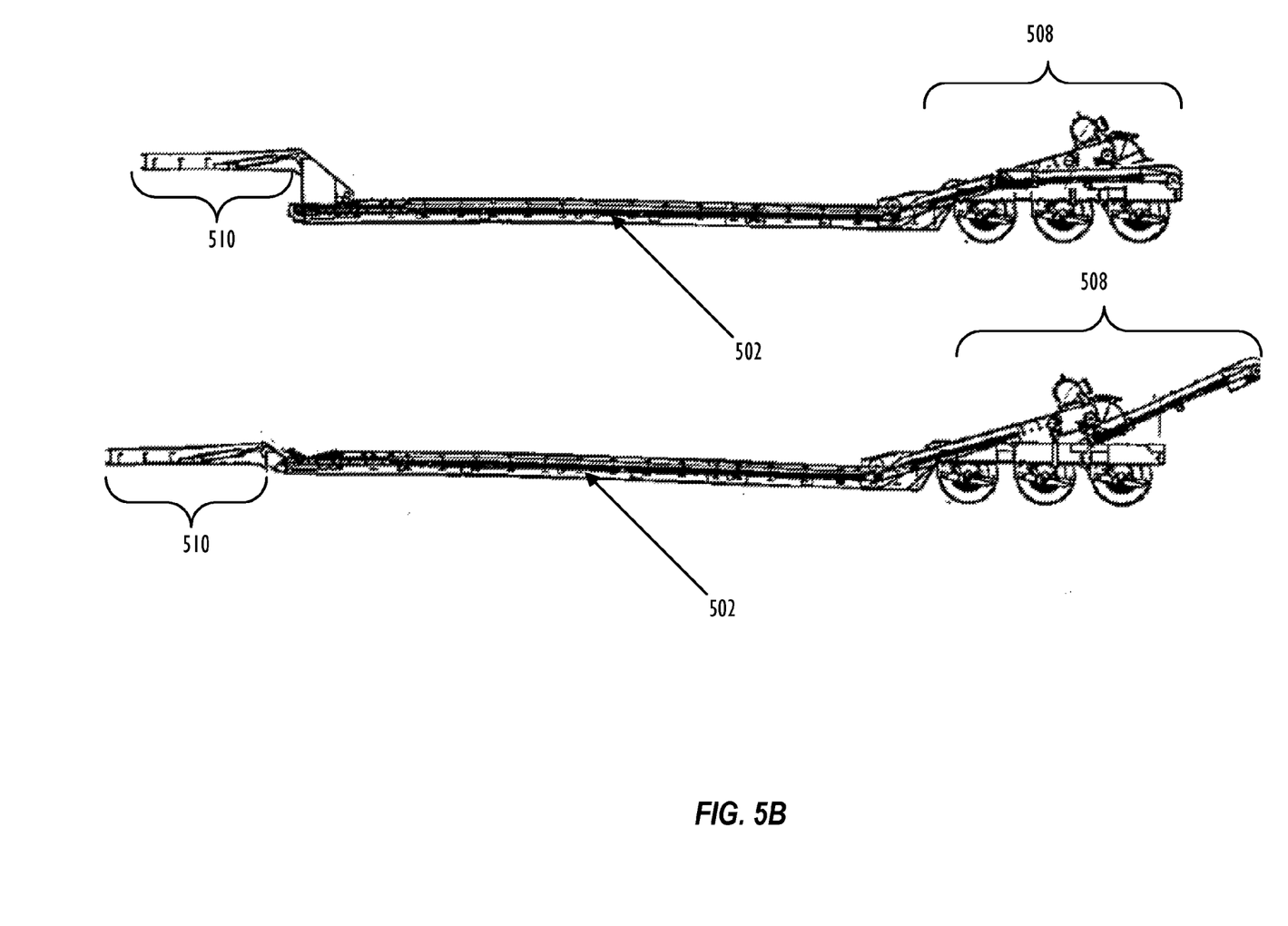
FIG. 5B illustrates a side view of an embodiment of a mobile conveyor system adapted to allow fracture sand transports to drive up to and directly load fracturing sand onto the mobile conveyor system.

FIGS. 5A and 5B are schematic diagrams of an embodiment of a mobile conveyor system 500 adapted to allow fracture sand transports to drive up to and directly load fracturing sand onto the mobile conveyor system 500. FIG. 5A provides a top down view of the mobile conveyor system 500, and FIG. 5B provides a side view of the mobile conveyor system 500. As shown in FIG. 5A, the mobile conveyor system 500 includes conveyor ramps/walls 506 that can be positioned in different orientations depending on the operation modes. In transportation mode, the conveyor ramps/walls 506 may be moved to and fastened at a substantially vertical position. In a sand loading operation mode, the conveyor ramps/walls 506 are laid down flat so that fracture sand transports are able to drive up to the mobile conveyor system 500 and load the fracturing sand onto the mobile conveyor system's 500 platform. In a sand transferring operation mode, the conveyor ramps/walls 506 may be configured at an angled position (e.g., at an angle less than the vertical position) and vibrate to move sand onto to the mobile conveyor system's 500 platform.

During sand transferring operation mode, the mobile conveyor system's 500 platform includes a hopper 504 that funnels the fracturing sand to the conveyor transport component 502 (e.g., a conveyor belt, augers, etc.). The conveyor transport component 502 then moves the fracturing sand to a conveyor assembly 508, which then transports the fracturing sand to a surge tank. In FIGS. 5A and 5B, one or more portions of the conveyor assembly 508 may be adapted to disconnect and move to a side-by-side position in transportation mode, and then subsequently connect and move to an extended position in operation mode. FIG. 5B also illustrates that the trailer connection component 510 may be detachable and/or configured to dropped to a lower vertical position so that fracturing sand transports are able to drive up and load the fracturing sand onto the mobile conveyor system's 500 platform during sand transferring operation mode.

Figure 6:
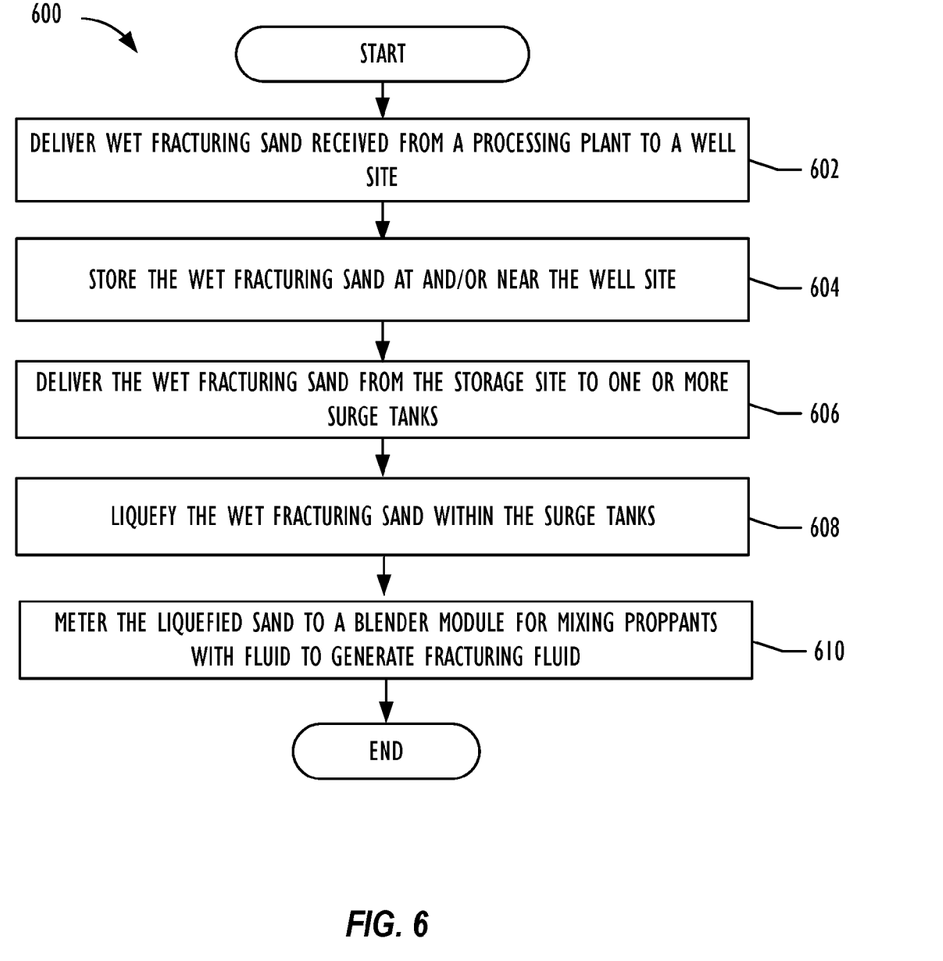
FIG. 6 is a flow chart of an embodiment of a method to provide and utilize wet fracturing sand for hydraulic fracturing.

FIG. 6 is a flow chart of an embodiment of a method 600 to provide and utilize wet fracturing sand for hydraulic fracturing. Method 600 may start at block 602 by delivering wet fracturing sand received from a processing plant to a well site. In one embodiment, method 600 may deliver the wet fracturing sand without using specialized transport (e.g., dry bulk tank trailers) or transportation containers designed to prevent exposure of rain, moisture, and/or other environmental factors that could impact the dryness level of the fracturing sand. For example, method 600 may use uncovered containers and conventional dump trucks with an open-box bed. Method 600 may then move to block 604 and store the wet fracturing sand at and/or near the well site. At block 604, method 600 may store the fracturing sand without using specialized storage facilities and/or containers (e.g., storage silos) that maintain dryness of the fracturing sand. To prevent the generation of silica dust, which the inhalation may lead to chronic personal injury and/or cause disability or death, method 600 may use a liquid spray system to maintain a pre-determined moisture level range for the wet fracturing sand.

Method 600 continues to block 606 and delivers the wet fracturing sand from the storage site to one or more surge tanks. In one embodiment, method 600 may transport the wet fracturing sand using mechanical means (e.g. front end loaders and/or conveyor systems). The conveyor system may be used to provide a steady and consistent flow of the wet fracturing sand into the surge tanks. Afterwards, method 600 moves to block 608 and liquefies the wet fracturing sand within the surge tanks. In one embodiment, method 600 liquefies the wet fracturing sand by using a plurality of vibration components that reduce clumping of the wet fracturing sand by breaking bonds (e.g., cohesion bonds) between water and the fracturing sand particles. In another embodiment, the method 600 liquefies the wet fracturing sand by generating and projecting sound waves (e.g., frequency can vary being subsonic, sonic or ultrasonic waves) into the wet fracturing sand collected within the surge tanks to break apart bonds between water and/or the fracturing sand particles. Method 600 then moves to block 610 and meters the liquefied sand to a blender module for mixing proppants with fluid to generate fracturing fluid. Method 600 may meter and control the amount of liquefied sand using a metering system (e.g., one or more augers).

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations may be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). The use of the term "about" means±10% of the subsequent number, unless otherwise stated.

Use of the term "optionally" with respect to any element of a claim means that the element is required, or alternatively, the element is not required, both alternatives being within the scope of the claim. Use of broader terms such as comprises, includes, and having may be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise.

What is claimed is:

1. A system for utilizing wet fracturing sand when creating fracturing fluid, comprising:
    a surge tank mounted on a trailer and configured to receive wet fracturing sand;
    a spray component located within the surge tank and configured to output a liquid to maintain a predetermined amount of the liquid within the surge tank to regulate moisture content of the wet fracturing sand;
    at least one vibration component disposed with the surge tank and configured to vibrate the wet fracturing sand received by the surge tank to generate liquefied wet fracturing sand; and
    a metering system coupled to the surge tank and mounted on the trailer, wherein the metering system is configured to:
        receive the liquefied wet fracturing sand from the surge tank; and
        control an amount of the liquefied wet fracturing sand outputted to a blending tub that produces a fracturing fluid, wherein the amount of the liquefied wet fracturing sand outputted to the blending tub affects an overall proppant concentration within the fracturing fluid.

2. The system of claim 1, further comprising a vibration isolation system coupled to a base of the surge tank, wherein the vibration isolation system includes one or more vibration isolators coupled between the surge tank and a structure base that connects to the trailer.

3. The system of claim 2, wherein the one or more vibration isolators include at least one of a spring, an air bag, or a rubber-based dampener.

4. The system of claim 1, wherein the at least one vibration component is mounted at a base of the surge tank and generates mechanical vibration at the base of the surge tank.

5. The system of claim 1, wherein the at least one vibration component is a vibration screen positioned at an opening of the surge tank where the wet fracturing sand enters the surge tank.

6. The system of claim 1, further comprising the blending tub mounted on the trailer, wherein the blending tub is coupled to the metering system and configured to mix the liquefied wet fracturing sand with a fluid to generate the fracturing fluid.

7. The system of claim 1, wherein the at least one vibration component is positioned within the surge tank and generates sound waves that traverse and vibrate the wet fracturing sand.

8. The system of claim 1, wherein the at least one vibration component is mounted on top of the surge tank.

9. The system of claim 1, wherein the surge tank is configured to synchronize with a conveyor system to receive the wet fracturing sand at a predetermined rate associated with a pump rate for pumping fracturing fluid into a wellbore.

10. The system of claim 1, further comprising a spray bar affixed to a top opening of the surge tank, wherein the spray bar is configured to output a liquid to regulate the moisture content for the wet fracturing sand.

11. The system of claim 1, wherein the surge tank is configured to receive wet fracturing sand at a rate greater than 20,000 pounds of sand per minute.

12. An apparatus for utilizing wet fracturing sand when creating fracturing fluid comprising:
    a surge tank mounted on a transport that receives wet fracturing sand;
    a spray component located within the surge tank, comprising a perforated piping that outputs a liquid, wherein the perforated piping is configured to maintain a predetermined amount of the liquid within the surge tank to regulate moisture content of the wet fracturing sand;
    a vibration component affixed to an outer surface of the surge tank to cause vibration of the received wet fracturing sand to generate liquefied wet fracturing sand; and
    an auger coupled to the surge tank and mounted on the transport, wherein the auger meters the liquefied wet fracturing sand into a blending tub that produces a fracturing fluid, wherein an amount of the liquefied wet fracturing sand outputted to the blending tub affects an overall proppant concentration within the fracturing fluid.

13. The surge tank of claim 12, further comprising a spray bar located at a top opening of the surge tank to introduce liquid to regulate the moisture content of the wet fracturing sand.

14. The surge tank of claim 12, further comprising a second vibration component affixed within the surge tank and configured to generate sound waves that travel through and liquefies the wet fracturing sand.

15. A system for utilizing wet fracturing sand when creating fracturing fluid, comprising:
    a surge tank for receiving wet fracturing sand;
    a means for outputting a liquid onto the received wet fracturing sand within the surge tank to regulate moisture content of the wet fracturing sand;
    a means for vibrating the received wet fracturing sand to liquefy the wet fracturing sand received within the surge tank; and
    a means for metering a controlled amount of the liquefied wet fracturing sand from the surge tank to a blending tub that produces a fracturing fluid, wherein the controlled amount of the liquefied wet fracturing sand metered into the blending tub affects an overall proppant concentration of the fracturing fluid pumped into a wellbore.

16. The system of claim 15, wherein the means for vibrating the received wet fracturing sand comprises means for mechanically vibrating the surge tank.

17. The system of claim 15, further comprising a bulk storage tank positioned above and coupled to the surge tank, wherein the surge tank receives the wet fracturing sand from the bulk storage tank and a means for vibrating the wet fracturing sand within the bulk storage tank.

18. The system of claim 15, wherein the means for vibrating the received wet fracturing sand comprises means for generating and directing sound waves into the wet fracturing sand to vibrate the wet fracturing sand.

19. The system of claim 15, wherein the surge tank is configured to receive wet fracturing sand at a rate greater than 20,000 pounds of sand per minute.

20. The system of claim 15, wherein the means for outputting the liquid comprises a means for maintaining a predetermined amount of the liquid within the surge tank.

* * * * *